United States Patent [19]

Siragusa

[11] 4,034,084

[45] July 5, 1977

[54] METHOD OF INHIBITING MICROBIAL ACTIVITY USING INSOLUBLE DIALDEHYDE POLYSACCHARIDES

[75] Inventor: Judith Ann Siragusa, Hopewell, N.J.

[73] Assignee: Personal Products Company, Milltown, N.J.

[22] Filed: Nov. 24, 1975

[21] Appl. No.: 634,704

Related U.S. Application Data

[63] Continuation-in-part of Ser. No. 513,678, Oct. 10, 1974, abandoned.

[52] U.S. Cl. ............................................. 424/180
[51] Int. Cl.² ................... A01N 9/00; A61K 31/70; A61L 13/00
[58] Field of Search .................................. 424/180

[56] References Cited

UNITED STATES PATENTS

| | | | |
|---|---|---|---|
| 3,086,969 | 4/1963 | Slager | 260/209 |
| 3,679,792 | 7/1972 | Litchfield | 424/48 |

Primary Examiner—Leonard Schenkman
Attorney, Agent, or Firm—Jason Lipow

[57] ABSTRACT

Microbial growth is inhibited in a medium susceptible to such growth by treatment with an effective amount of an insoluble dialdehyde polysaccharide which is sufficient to maintain an insoluble aldehyde content in the medium of at least about 0.1 weight percent. The insoluble dialdehyde polysaccharide does not exert a systematic effect on the medium. Suitable dialdehyde polysaccharides for this purpose are insoluble dialdehyde starch, dialdehyde cellulose, and the like.

16 Claims, No Drawings

METHOD OF INHIBITING MICROBIAL ACTIVITY USING INSOLUBLE DIALDEHYDE POLYSACCHARIDES

This application is a continuation in part of my copending application, Ser. No. 513,678 filed on Oct. 10, 1974, now abandoned.

BACKGROUND OF THE INVENTION

This invention relates to methods for inhibiting microbial activity. In particular, this invention relates to methods utilizing antimicrobial agents which are insoluble in aqueous media.

U.S. Pat. No. 2,801,216 discloses that certain saturated lower dialdehydes possess bactericidal activity toward sulfate-reducing bacteria. Also, alcoholic sporicidal compositions containing similar saturated lower dialdehydes are taught in U.S. Pat. No. 3,016,328. In addition, it is taught in U.S. Pat. No. 3,679,792 that water-soluble dialdehyde starch can be incorporated into chewing gum compositions as a cariostatic agent which is released into the oral cavity upon mastication. In all of the foregoing instances the bactericidal or sporicidal agent is soluble and readily enters the medium which is susceptible to microbial growth. It has now been discovered, however, that effective inhibition of microbial activity can be achieved by means of dialdehyde polysaccharides which are not soluble in the growth medium and thus do not exert a systemic effect on the medium.

SUMMARY OF THE INVENTION

The present invention contemplates applying to a locus susceptible to microbial growth an effective amount of an insolubkle dialdehyde polysaccharide sufficient to maintain an insoluble dialdehyde polysaccharide sufficient to maintain an insoluble aldehyde content in the medium of at least about 0.1 weight percent. Microbial activity in wounds or lesions can be inhibited by topical treatment of the affected area with the aforesaid dialdehyde polysaccharide. Particularly preferred active ingredients for the purposes of the present invention are insoluble dialdehyde starch and dialdehyde cellulose having about 15 to about 100 percent of the 2,3-hydroxyl groups thereof oxidized to dialdehyde groups, that is, the insoluble dialdehyde polysaccharide contains at least about 6 weight percent aldehyde groups, based on the dialdehyde polysaccharide.

DETAILED DESCRIPTION OF THE PREFERRED EMBODIMENTS

It has been found that water-insoluble dialdehyde polysaccharides such as water-insoluble dialdehyde starch and dialdehyde cellulose inhibit the growth of microorganisms with which these polysaccharides come in contact. Unlike other known antimicrobial agents which dissolve in or diffuse throughout a medium capable of sustaining microbial activity, the water-insoluble dialdehyde polysaccharides do not become part of the growth medium and thus do not alter the ecology thereof. This is a very desirable property because the antimicrobial agent thus does not enter the host system and is not absorbed by the host or by individuals who manufacture and/or administer the antimicrobial agents.

The water-insoluble dialdehyde polysaccharides can be incorporated into surgical or burn dressings, adhesive bandages, sanitary napkins, tampons, incontinence pads, disposable mattress pads, and can also be applied as a powder directly to an open wound or lesion. Furthermore, inasmuch as an inhibition of bacterial growth prevents the formation of malodors which are the normal metabolic products of growing microorganisms, the present method also provides a simultaneous deodorant effect.

The invention may be employed in inhibiting the growth of bacteria in vitro or in animals (for the purposes herein the term animals includes members of the animal kingdom including, for example, humans). In the case of in vitro use the water insoluble dialdehyde polysaccharides may be homogeneously distributed throughout the medium or may be employed in contact with a surface of the medium. In the case of animals the dialdehyde polysaccharides may be administered topically or alternatively may even be administered orally. For example, when the inhibition of bacterial growth is directed toward preventing the formation of malodorous metabolic products in animals and in particular as a deodorant in humans, the dialdehyde polysaccharides may be employed in the form which deodorants are commonly found, e.g., in the form of a dusting powder or compounded with other ingredients in the form of a lotion, cream, stick or even spray-on deodorant.

Suitable dialdehyde polysaccharides for the purposes of the present invention can be prepared by the selective oxidation of the 2,3-hydroxyl groups on the glucose units which make up the polysaccharide chain. Preferably, at least about 15 percent of the hydroxyl groups are oxidized, and more preferably about 35 to about 100 percent of the hydroxyl groups are oxidized. Inasmuch as the present invention contemplates water-insoluble dialdehyde polysaccharides, the degree of polymerization of the polysaccharide should be at least about 50 repeating units per molecule.

Methods for the aforesaid selective oxidation of polysaccharides to dialdehyde polysaccharides are known in the art. A particularly convenient method for this purpose involves oxidation by means of periodic acid as taught in U.S. Pat. No. 3,086,969 to Slager. According to this method, a polysaccharide is reacted with a solution of periodic acid having a concentration of at least about 10 weight percent, based on the total amount of reactants present, in the presence of a strong acid which maintains the hydrogen ion concentration of the periodic acid solution at a pH below about 1.0. The reaction temperature usually is about 30° C. to 35° C.

The inhibition of microbial activity by the present method has been demonstrated in vitro and in vivo. The experimental results are reported hereinbelow.

Various samples of a quantity of polysaccharide powder comprising aldehyde polysaccharide are subjected to a variety of pretreatment steps and then each sample is added to molten nutrient agar at about 45° C. Each of the resulting admixtures is then dispensed onto sterile Petri plates and permitted to solidify. The surface of each solidifed mixture is cross-streaked with about 0.01 milliliter aliquots of 18-hour broth cultures of various microbes constituting a broad spectrum which included both Gram positive and Gram negative Bacteria. Nutrient agar plates without any aldehyde polysaccharide powder are cross-streaked with the same broth culture and serve as controls. The inoculated plates are then incubated for 18 to 24 hours at a temperature of about 37° C. and examined to determine maximum growth of the test organisms. The samples of polysaccharide powder and the nature of their pretreatment are identified in Table 1 and the test results are reported in Table 2. The materials identified as cellulosic dialdehyde polysaccharides are prepared from ground woodpulp having an approximate degree of polymerization ranging from 500 to 2100. The materials identified as starch dialdehyde polysaccharides are prepared from waxy maize cornstarch having a degree of polymerization of about 1000. The resulting aldehyde polysaccharides have essentially the same degree of polymerization as the starting materials and are water insoluble.

The data in these tables show that broad spectrum antimicrobial activity against both Gram negative and Gram positive Bacteria was present as long as the total aldehyde content of the test system is about 1.5 weight percent or more, and that Gram positive microorganisms are inhibited when as little as about 0.1 to 0.2 weight percent of the aldehydic material is present in the test system.

The data further shows that the antimicrobial activity of the dialdehyde polysaccharides is not lost by heating, washing in cold water, hot water, or with detergent.

TABLE 1

IDENTIFICATION OF POLYSACCHARIDE SAMPLE

| SAMPLE | COMPOSITION | PERCENT ALDEHYDE [1] IN DIALDEHYDE COMPONENT | PRETREATMENT |
|---|---|---|---|
| A | 0.5 gm. dialdehyde starch | 90 | Air dried to constant weight |
| B | 0.5 gm. dialdehyde cellulose | 85 | '' |
| C | 1.0 gm. dialdehyde cellulose | 35 | '' |
| D | 0.5 gm. dialdehyde cellulose | 66 | '' |
| E | '' | 66 | '' |
| F | '' | 66 | '' |
| G | '' | 66 | Cold water washed and air dried |
| H | '' | 54 | Air Dried to constant weight |
| I | '' | 54 | Cold water washed and air dried |
| J | '' | 54 | Dried at 100° C to constant weight |
| K | '' | 54 | Dried at 150° C to constant weight |
| L | '' | 54 | Hot water washed and air dried |
| M | '' | 54 | Hot water washed and dried at 100° C |
| N | '' | 54 | Detergent washed and air dried |
| O | 0.25 gm. wood pulp [2] and 0.25 gm. dialdehyde cellulose | 80 | Blended and air dried |
| P | 0.5 gm. dialdehyde cellulose | 35 | Air dried to constant weight |
| Q | 0.25 gm. wood pulp [2] and 0.25 gm. dialdehyde cellulose | 66 | Blended and air dried |
| R | '' | 54 | '' |
| S | 0.5 gm. dialdehyde cellulose | 19 | Air dried to constant weight |
| T | '' | 10 | '' |
| U | 0.25 gm. wood pulp [3] and 0.25 gm. dialdehyde cellulose | 10 | Blended and air dried |
| V | 0.38 gm. wood pulp [3] and 0.12 gm. dialdehyde cellulose | 10 | '' |
| W | 0.43 gm. wood pulp [3] and 0.07 gm. dialdehyde cellulose | 10 | '' |
| X | 0.47 gm. wood pulp [3] and 0.03 gm. dialdehyde cellulose | 10 | '' |
| Y | 0.50 gm. wood pulp [2] | 0 | Air dried to constant weight |
| Z | 0.50 gm. wood pulp [3] | 0 | '' |

[1] percent aldehyde refers to percent of 2, 3 hydroxyl groups which have been oxidized based on total polysaccharide in the sample.
[2] fully bleached Southern Pine kraft pulp (fluff) obtained from Buckeye Cellulose Co.
[3] bleached chemical wood pulp, finely ground (particle size 50–70 microns) obtained from Brown Co., Berlin, N.H., sold by them under tradename Solka-floc.

TABLE 2

SUMMARY OF ANTIMICROBIAL SCREENING

| Sample | Aldehyde Concentration [1] in Test System | Organisms Treated | | | | |
|---|---|---|---|---|---|---|
| | | P.mirabilis | S.aureus | St.fecalis | E.coli | A.aerogenes |
| A | 4.3 | N.T. | + | + | 0 | 0 |
| B | 4.0 | +N.T | N.T | N.T | N.T | |
| C | 3.2 | N.T | + | + | + | + |
| D | 3.1 | N.T | + | + | + | + |
| E | 3.1 | + | + | + | + | + |
| F | 3.1 | + | + | + | + | + |
| G | 3.1 | N.T | + | + | + | + |
| H | 2.6 | N.T | + | + | + | + |
| I | 2.6 | N.T | + | + | + | + |
| J | 2.6 | N.T | + | + | + | + |
| K | 2.6 | N.T | + | + | + | + |
| L | 2.6 | + | + | + | + | + |
| M | 2.6 | + | + | + | + | + |
| N | 2.6 | + | + | + | + | ± |
| O | 1.9 | N.T | + | + | + | + |
| P | 1.7 | N.T | + | + | + | ± |
| Q | 1.6 | N.T | + | + | + | 0 |
| R | 1.3 | + | + | + | 0 | + |
| S | 0.9 | + | + | + | 0 | 0 |
| T | 0.5 | 0 | + | + | 0 | 0 |
| U | 0.25 | N.T | + | + | 0 | 0 |
| V | 0.12 | N.T | + | + | 0 | 0 |
| W | 0.062 | N.T | 0 | 0 | 0 | 0 |
| X | 0.031 | N.T | 0 | 0 | 0 | 0 |
| Y | 0.0 | 0 | 0 | 0 | 0 | 0 |

TABLE 2-continued

SUMMARY OF ANTIMICROBIAL SCREENING

| Sample | Aldehyde Concentration[1] in Test System | Organisms Treated | | | | |
|---|---|---|---|---|---|---|
| | | P.mirabilis | S.aureous | St.fecalis | E.coli | A.aerogenes |
| Z | 0.0 | N.T | 0 | 0 | 0 | 0 |

+ = total inhibition;
± = slight inhibition;
0 = no inhibition;
N.T. = not tested

[1]aldehyde concentration is calculated on the basis of the reported aldehyde content of the test material as a function of the total weight of test sample plus nutrient agar.

EXAMPLE 2

Antibacterial Paper dressing

A paper handsheet was prepared from a blend of dialdehyde cellulose (50 weight percent dialdehyde cellulose [80% aldehyde] and 50 weight percent wood pulp).

Petri plates containing 10 ml. of Trypticase soy agar were prepared with the agar surface cross-streaked with test bacteria including S. aureus and P. mirabilis. A square piece of the test hand sheet (1 inch × 1 inch) was then placed onto the innoculated agar surface and incubated for about 18 to 24 hours. Surface inhibition of S. aureus and P. mirabilis was observed, as well as a slight zone of inhibition against S. aureus.

EXAMPLE 3

Wound Treatment with Dialdehyde Cellulose

The tails of three newborn Pembroke Welsh Corgi puppies were amputated. Two days later, two of the puppies were observed to have an infection in the amputated region. A bloody purulent discharge, as well as swelling of the tail stump was noted. Hot compresses were applied to the infected area at regular intervals for about one day, but no improvement was observed. Thereafter, dialdehyde cellulose powder (80% aldehyde; particle size about 60 to 80 microns) was sprinkled onto the stump of one of the puppies while the other received no further treatment. One day later the dialdehyde cellulose-treated stump was no longer swollen or moist, and the flesh had a clean appearance. The untreated stump, on the other hand, was still swollen and moist, and the same purulent exudate was present.

EXAMPLE 4

Washing of Dialdehyde Cellulose

A sample of dialdehyde cellulose (Sample H) was washed under various conditions as shown in Table 3 below, and the obtained washings were tested for antimicrobial activity in a manner similar to Example 1 above. No inhibition of bacterial growth by the washings was observed. Thus, the sterilizing properties of the dialdehyde polysaccharides are indigenous to the water-insoluble oxidized polysaccharide itself.

TABLE 3

WATER WASHING EXPERIMENTS WITH DIALDEHYDE CELLULOSE*

| Wt. of Sample (grams) | Volume of Water (ml) | Length of Time (hours) | Temperature (° C.) | Apparatus Used |
|---|---|---|---|---|
| 0.5 | 5 | 0.16 | 20 | Beaker with stirrer |
| 7.0 | 200 | 7.00 | 100 | Soxhlet extracter |
| 0.5 | 5 | 20.00 | 20 | Beaker with stirrer |

*Sample H

I claim:

1. A method for inhibiting bacterial growth in a locus susceptible to bacterial growth comprising applying to said locus a bactericidally effective amount of a water-insoluble dialdehyde polysaccharide selected from the group consisting of dialdehyde cellulose and dialdehyde starch wherein said water-insoluble dialdehyde polysaccharide has a degree of polymerization of at least about 50 repeating units per molecule.

2. The method of claim 1 wherein said water-insoluble dialdehyde polysaccharide is applied to said medium in an amount sufficient to maintain an insoluble aldehyde polysaccharide content in said medium of at least about 0.1 weight percent.

3. The method of claim 2 wherein said water-insoluble dialdehyde polysaccharide is applied to said medium in an amount sufficient to maintain an insoluble aldehyde polysaccharide content in said medium of at least about 1.5 weight percent.

4. The method of claim 1 wherein said water-insoluble dialdehyde polysaccharide contains at least about 6 weight percent aldehyde groups, based on the weight of said dialdehyde polysaccharide.

5. The method of claim 1 wherein said water-insoluble dialdehyde polysaccharide is water-insoluble dialdehyde starch.

6. The method of claim 1 wherein said water-insoluble dialdehyde polysaccharide is water-insoluble dialdehyde cellulose.

7. A method of inhibiting bacterial growth in an in vitro medium susceptible to bacterial growth comprising applying to said medium a bactericidally effective amount of a water-in-soluble dialdehyde polysaccharide selected from the group consisting of dialdehyde cellulose and dialdehyde starch wherein said water-insoluble dialdehyde polysaccharide has a degree of polymerization of at least about 50 repeating units per molecule.

8. The method of claim 7 wherein said water-insoluble dialdehyde polysaccharide is applied to said medium in an amount sufficient to maintain an insoluble aldehyde polysaccharide content in said medium of at least about 0.1 weight percent.

9. The method of claim 8 wherein said water-insoluble dialdehyde polysaccharide is applied to said medium in an amount sufficient to maintain an insoluble aldehyde polysaccharide content in said medium of at least about 1.5 weight percent.

10. The method of claim 7 wherein said water-insoluble dialdehyde polysaccharide contains at least about 6 weight percent aldehyde groups, based on the weight of said dialdehyde polysaccharide.

11. The method of claim 7 wherein said water-insoluble dialdehyde polysaccharide is water-insoluble dialdehyde starch.

12. The method of claim 7 wherein said water-insoluble dialdehyde polysaccharide is water-insoluble dialdehyde cellulose.

13. A method of inhibiting bacterial growth on an animal and the malodor associated therewith comprising topically administering to said animal a bactericidally effective amount of a water-insoluble dialdehyde polysaccharide selected from the group consisting of dialdehyde cellulose and dialdehyde starch wherein said water-insoluble dialdehyde polysaccharide has a degree of polymerization of at least about 50 repeating units per molecule.

14. The method of claim 13 wherein said water-insoluble dialdehyde polysaccharide contains at least about 6 weight percent aldehyde groups, based on the weight of said dialdehyde polysaccharide.

15. The method of claim 13 wherein said water-insoluble dialdehyde polysaccharide is water-insoluble dialdehyde starch.

16. The method of claim 13 wherein said water-insoluble dialdehyde polysaccharide is water-insoluble dialdehyde cellulose.

* * * * *